United States Patent [19]

Henry

[11] 4,049,496
[45] Sept. 20, 1977

[54] RAPID SEPARATION OF PLASMA CREATINE KINASE ISOENZYMES

[76] Inventor: Philip D. Henry, 832 Bricken, Kirkwood, Mo. 63122

[21] Appl. No.: 749,064

[22] Filed: Dec. 9, 1976

Related U.S. Application Data

[63] Continuation-in-part of Ser. No. 690,556, May 27, 1976, abandoned.

[51] Int. Cl.$^2$ .................. C07G 7/02; C12K 1/00
[52] U.S. Cl. .................. 195/66 R; 195/103.5 R
[58] Field of Search .................. 195/66 R, 103.5 R

[56] References Cited
U.S. PATENT DOCUMENTS 3,994,783  11/1976  Rao et al. .................. 195/103.5 R

OTHER PUBLICATIONS

Mercer, Clinical Chemistry, vol. 20, No. 1, 1974, pp. 36–40.
Bondar et al., Clinical Chemistry, vol. 22, No. 4, 1976, pp. 552–556.

Primary Examiner—Lionel M. Shapiro
Attorney, Agent, or Firm—Koenig, Senniger, Powers and Leavitt

[57] ABSTRACT

An improved method for the rapid separation of the MM and MB creatine kinase isoenzymes is provided. The method involves the use of an ion exchange support material comprising porous glass beads having a stationary phase coupled to the surfaces thereof through an intermediate coupling agent. The intermediate coupling agent is preferably a silane coupling agent constituted by an organosilane with a silicon functional group capable of bonding to the surfaces of the glass beads and an organic functional group capable of bonding to the stationary phase. Less preferably, the coupling agent may be formed from a Grignard reagent of the formula RMgX where R is lower alkenyl and X is halogen. A blood plasma or serum sample and a buffer of low ionic strength are contacted with the ion exchange support, the resultant mixture is incubated to effect MB isoenzyme adsorption by the support, the supernatant liquid fraction containing the MM isoenzyme is separated from the support, the support is washed to effect a removal of residual of MM therefrom, a buffered solution of a strong electrolyte is added to the support to effect desorption of the MB isoenzyme therefrom and the supernatant liquid fraction containing the MB isoenzyme is separated from the support. The MM and MB activity in the respective liquid fractions thus obtained is then assayed to provide an index of myocardial damage.

14 Claims, 5 Drawing Figures

RAPID SEPARATION OF PLASMA CREATINE KINASE ISOENZYMES

CROSS-REFERENCE TO RELATED APPLICATION

This application is a continuation-in-part of my application Ser. No. 690,556, filed May 27, 1976 now abandoned.

BACKGROUND OF THE INVENTION

This invention relates to the field of clinical chemistry and, more particularly, to an in vitro method for the rapid separation of the MM and MB creatine kinase isoenzymes in blood plasma or serum and for determining the relative activities of the separated isoenzymes.

Three serum creatine phosphokinase (CPK) isoenzymes (MM, MB and BB) have been recognized in tissue extracts and plasma. Myocardium is richly endowed with the MB CPK isoenzyme. Accordingly, increased serum MB CPK activity reflects myocardial injury.

Plasma from normal subjects contains mainly the MM isoenzyme; the MB form accounts for less than 5% of the total plasma activity and activity attributable to BB is negligible, Am. J. Cardiol. 33, 650 (1974). MB activity increases after myocardial infarction, and the magnitude of the increase appears to reflect the extent of myocardial injury. No increase in MB activity is observed after intramuscular injections or after operations not involving the heart. Because of its relative specificity as an index of myocardial damage, a rapid, quantitative assay of MB activity would be particularly useful.

In the prior art, the methods employed to measure the activities of these isoenzymes have been based on electrophoretic (Am. J. Cardiol. 33, 650 (1974) or column chromatographic (Clin. Chem. Acta. 38, 285 (1972)) procedures, which are somewhat complex for routine clinical use. Also in the prior art is a procedure (Clin. Chem. 20, 36 (1974)) utilizing a gel (marketed under the trade designation "DEAE Sephadex A50" by Pharmacia) which suffers from numerous shortcomings. This procedure, for example, entails the handling of small amounts of moist gel and tedious and repeated centrifugations to remove residual MM isoenzyme before desorbing the MB isoenzyme. Further, the procedure requires the production of columns that yield acceptably fast flow rates, stepwise elution, and fractionated collection. Also, one milliliter of plasma is required for each determination.

Thus, while recent advances have facilitated detection of CPK isoenzymes, available techniques have unavoidable quantitative and procedural limitations. There has remained, therefore, a need for a simple, rapid procedure for the quantitation of creatine kinase isoenzymes in blood plasma or serum.

SUMMARY OF THE INVENTION

Among the objects of the present invention may be noted the provision of a rapid, simple and convenient method for the separation of MM and MB creatine kinase isoenzymes in blood plasma or serum and for determining the relative activities of the separated isoenzymes; the provision of such a method in which the separative steps may be performed in a single test tube thereby obviating losses caused by transfer of test material; the provision of a method of the type described in which an ion exchange support material comprising porous glass beads of a specified nature are advantageously employed; and the provision of such a method in which the MB isoenzyme is quantitatively adsorbed to the ion exchange support material while the MM isoenzyme remains free in solution. Other objects and features will be in part apparent and in part pointed out hereinafter.

The present invention is thus directed to an in vitro method for effecting rapid separation of the MM and MB creatine kinase isoenzymes in blood plasma or serum and for determining the relative activities of the thus separated isoenzymes. The method involves the steps of contacting a blood plasma or serum sample and a buffer of low ionic strength with an ion exchange support comprising porous glass beads having a stationary phase coupled to the surfaces thereof through an intermediate coupling agent, incubating the resultant mixture to effect MB isoenzyme adsorption by said support, separating the supernatant liquid fraction containing the MM isoenzyme from said support, washing the support to effect removal of residual MM, adding a buffered solution of a strong electrolyte to said support to effect desorption of the MB isoenzyme therefrom, separating the supernatant liquid fraction containing the MB isoenzyme from said support, and assaying the MM and MB activity in the respective liquid fractions thus obtained.

DESCRIPTION OF THE PREFERRED EMBODIMENTS

Figure 1:
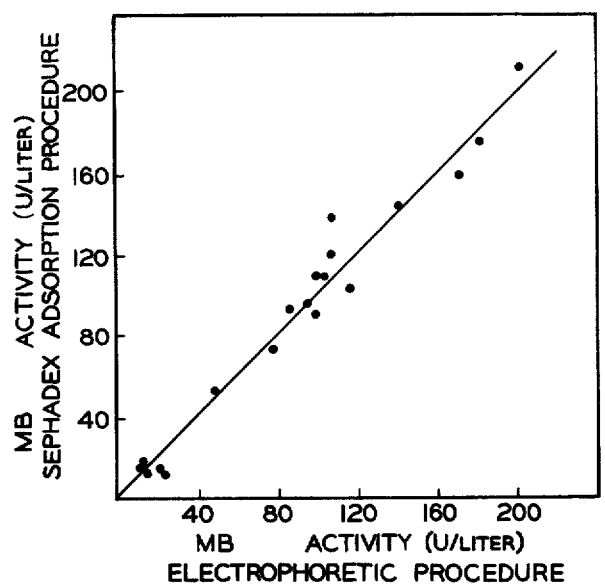
FIG. 1 is a graph illustrating the relationship between MB isoenzyme activity as measured by the electrophoretic kinetic procedure and MB isoenzyme activity as measured by the "DEAE Sephadex A50" gel adsorption procedure.

In accordance with the present invention, it has now been found that the blood plasma creatine kinase isoenzymes may be rapidly and reliably separated and the respective MM and MB activities determined through the employment of an ion exchange support comprising porous glass beads having a stationary phase coupled to the surfaces thereof through an intermediate coupling agent. It is highly preferable that the coupling agent be a silane coupling agent although less preferably the coupling agent may be formed from a Grignard reagent of the formula RMgX where R is lower alkenyl and X is halogen. More specifically and preferably, the invention involves the utilization of such an ion exchange support in which the intermediate silane coupling agent is constituted by an organosilane with a silicon functional group capable of bonding to the surfaces of the glass beads and an organic functional group capable of bonding to the stationary phase. The organic functional group may be a simple carbohydrate or carbohydrate derivative and preferably is glycerol. The intermediate organosilane coupling agent is preferably glycidoxypropyltrimethoxysilane, and the stationary phase is preferably derived from diethylamine or diethylaminoethanol.

In is broadest aspect, the present invention is directed to the method for effecting rapid separation of the MM and MB creatine kinase isoenzymes in blood plasma or serum and for determining the relative activities of the thus separated isoenzymes involving the steps of contacting a blood plasma or serum sample and a buffer of low ionic strength with an ion exchange support comprising porous glass beads having a stationary phase coupled to the surfaces thereof through an intermediate coupling agent, incubating the resultant mixture to effect MB isoenzyme adsorption by the said support, separating the supernatant liquid fraction containing the MM isoenzyme from the said support, washing the support to effect removal of residual MM, adding a buffered solution of a strong electrolyte to the said support to effect desorption of the MB isoenzyme therefrom, separating the supernatant liquid fraction containing the MB isoenzyme from the said support, and assaying the MM and MB activity in the respective liquid fractions thus obtained.

The procedure afforded by the present invention is simple, rapid and provides a means whereby all separative steps may be performed in a single test tube and can be completed within a few minutes. These features are of paramount importance in rapidly determining the extent of myocardial injury.

In contract to the prior art methods previously described, the ion exchange support (glass beads) materials used in the practice of the present invention require no preswelling as does the Sephadex gel type material adverted to above. Further, the glass beads described hereinafter may be dispensed dry, sediment quickly without centrifugation, do not stick to the wall of the test tubes and do not compact during filtration. Further, the glass beads can be stored dry and can be used immediately in contrast to many other chromatographic media.

The ion exchange support materials useful in the present invention may be characterized as embracing porous glass beads having a stationary phase coupled to the surfaces thereof through an intermediate coupling agent and preferably through an intermediate silane coupling agent. Structurally the silane coupling agent is an organosilane with a silicon function group capable of bonding to the support surface and an organic functional group capable of bonding to the stationary phase. This composite has the following general chemical formula:

wherein R is a simple carbohydrate or a carbohydrate derivative and $P_s$ is the stationary phase.

As stated, the preferred organosilane coupling agent is glycidoxypropyltrimethoxysilane, the preferred organic functional group is glycerol and the preferred stationary phase is derived from diethylamine or diethylaminoethanol. The glycidoxypropyltrimethoxysilane coupling agent becomes attached to the support accordingly to the following reaction:

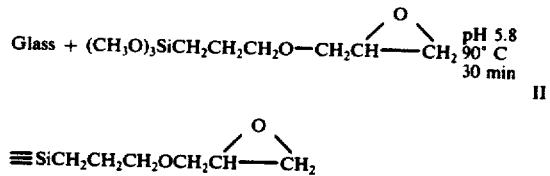

The glass is a commercial glass (marketed by Corning Glass, Corning porous glass code number 7930) whose composition is $SiO_2$—96%; $B_2O_3$—3%; and $Na_2O$—1%, Filbert, A.M., *Immobilized Enzymes for Industrial Reactors*, R. A. Messing (ed.) p. 39–61, Academic Press, New York (1975).

As an example, the glycidoxypropylsilyl support (II) above is prepared as follows: A 5% aqueous solution of the silylation reagent was prepared by adding glycidoxypropyltrimethoxysilane dropwise to water with constant stirring while keeping the pH of solution between 5.5 and 5.8 with $10^{-3}$ KOH. This silylation solution was added to a quantity of the above-noted inorganic support (glass beads) and vacuum applied to remove air from the pores. The silylation solution should have sufficient volume to cover all the support particles in the reaction flask. This slurry was heated to 90° C. for 30 minutes with swirling every 5 minutes. The support was then filtered, washed sequentially with water and acetone, prior to drying in vacuo.

Amine coupled anion exchange supports were prepared according to the following reactions (DEA meaning diethylamine and DEAE meaning diethylaminoethanol). Dimethylformamide (DMF) was used as the solvent in these reactions.

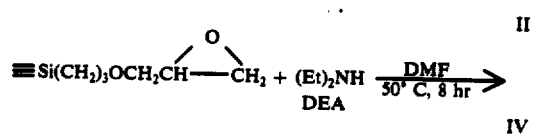

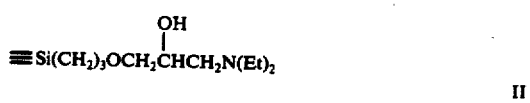

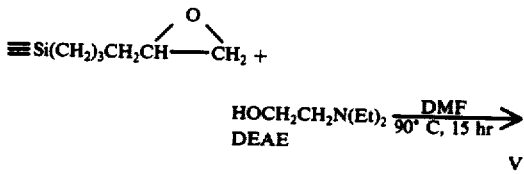

In the preparation of support IV, the DEA/DMF ratio is not critical. The ion exchange capacity of all the above supports were comparable when the concentration of DEA in the reaction was 10% or greater. The time needed for maximum incorporation of amine is approximately 8 hours when the reaction is carried out in 80% DEA solution at 50° C. Longer reaction time has no apparent effect on the ion exchange capacity of the final products.

In the preparation of the DEA and DEAE support materials IV and V, a quantity of the glycidoxypropylsilyl support II was added to a flask containing DEA or DEAE in dimethylformamide. The resulting slurry was swirled and left at ambient or elevated temperature for a fixed time. The resulting support was then washed with 500 ml. of water and acetone and then dried in vacuo. These supports have a high ion exchange capacity.

The above-prepared DEAE ion exchange support material is commercially available and is marketed under the trade designation "DEAE-Glycophase-G" by Corning Glassworks, Biological Products Department, Medfield, Mass. The diethylamine ion exchange support material is known as "DEA-Glycophase-G".

Ion exchange support materials of the type described above thus provide a hydrophilic, non-ionic carbohydrate monolayer which is covalently bonded, the carbohydrate phase covering the active sites of the glass support. These support materials are physically stable and do not shrink or swell with changes of pH, molarity or solvent. They exhibit superior and reproducible flow properties, and are easily cleaned and require no preswelling.

In a less preferable embodiment of the invention, the intermediate coupling agent may be formed from a Grignard reagent of the type RMgX where R is lower alkenyl and X is halogen. In an illustration of this embodiment of the invention, the hydroxyl group on the silaceous surface of the glass beads is chlorinated:

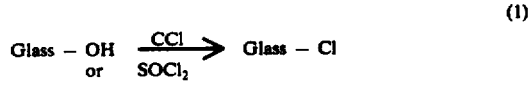

(1)

The Grignard reagent may be conventionally prepared as follows:

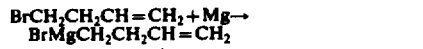

(2)

The Grignard reagent is reacted with the glass beads:

(3)

which is then converted as follows:

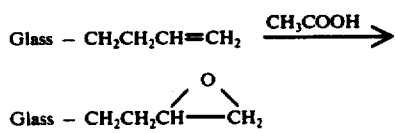

(4)

which is then reacted with DEAE as follows:

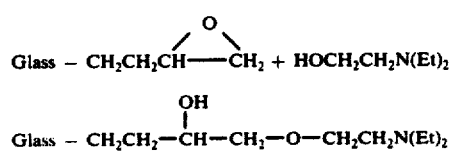

(5)

In carrying out the practice of the invention, ion exchange support material of the type described above in the form of glass beads is first contacted with a blood plasma or serum sample and a buffer of low ionic strength, i.e., a buffer containing no strong electrolyte such as sodium chloride. The buffer may, for example, consist of tris(hydroxymethyl) aminomethane (base), 100 mmol/liter, HCl, 56 mmol/liter (pH 8.0 at 22° C.); and dithiothreitol, 3 mmol/liter. Preferably, the pH of the low ionic strength buffer is between approximately 7.1 and 9.0.

The resultant mixture is then incubated for a short period (e.g., 3 minutes) to effect MB isoenzyme adsorption by the glass beads ion exchange support material. The supernatant liquid fraction containing the MM isoenzyme is then separated from the support material.

Following the separation step, the glass beads are washed to effect removal of residual MM therefrom. Several washing operations may be carried out whereby the removal of residual MM results in at least a 1000 fold dilution of MM activity in the initial blood plasma sample and desirably a 10,000 fold dilution of MM activity in the initial sample.

After the washing step, a buffered solution of a strong electrolyte is then added to the support to effect desorption of the MB isoenzyme therefrom. For this purpose, a buffer of the type described above additionally containing a strong electrolyte may be utilized. As the strong electrolyte, various materials may be employed including, for example, alkali metal halides, such as sodium and potassium chloride, and alkaline earth halides. Other strong electrolytes known to those skilled in the art may also be used. Preferably, the buffered solution has a ionic strength of between approximately 0.25 and 0.5 and the concentration of the strong electrolyte in the buffered solution ranges between 250 and 500 mmol/liter.

The supernatant liquid fraction containing the desorbed MB isoenzyme is then separated from the support material and the MM and MB activity in the respective liquid fractions obtained as described is assayed as by the kinetic fluorometric assay technique described hereinafter.

In carrying out the method of the invention as described, it is preferred but not essential to employ a filter sampler such as that marketed under the trade designation "Unichem" (by Unichem, Fairburn, Ga.). As will be evident from Example 1 hereinafter, the use of such a filter sampler facilitates and expedites the performance of the method and minimizes the necessity for transfer of test material.

The present invention thus provides a simple, rapid and convenient method for separating plasma or serum creatine kinase isoenzymes and determining the relative activities of the thus separated MM and MB isoenzymes. The entire separation procedure may be performed in a single test tube and as many as 60 samples can easily be fractionated within an hour. Moreover, for processing multiple samples, as many as 36 tubes and filter samplers on a rack may be processed simultaneously. The method of the present invention therefore possesses the advantages which render it suitable for routine clinical use.

In order to insure a rapid and complete description of MB isoenzyme from the anion exchanger support material, a concentration of strong electrolyte in the buffered solution as previously described is such that the BB isoenzyme is also desorbed. Thus, if present, BB activity would be added to the MB activity in the assay of the latter. This does not however appear to be a serious methodological shortcoming because BB activity is rarely demonstrable in human plasma, Anido et al., Diagnostic efficacy of myocardial creatine phosphokinase using polyacrylamide disk gel electrophoresis, Am. J. Clin. Pathol. 61, 599 (1974). Demonstrable BB activities have been reported in malignant hyperthermia with very high total activities (Anido et al., supra) and in one case of renal tubular necrosis (Smith, Separation of tissue and serum creatine kinase isoenzymes of polyacrylamide gel slabs. Clin. Chim. Acta 39, 351 (1972)). Theoretically, infarction or surgery of any organ rich in BB isoenzyme (brain, kidney, intestine, bladder, uterus) might be expected to yield increased BB activities. However, such events are usually not likely to be confused with acute myocardial infarction.

As shown by the experimental data presented hereinafter, the results of measurements of isoenzymes in plasma or serum samples from patients with acute myocardial infarction were compared to those obtained with an independent quantitative assay method previously reported in the prior art. Additional measurements were performed on standard plasma or serum samples containing mixtures of MM and MB isoenzymes purified from human myocardium. The results by the differrent procedures agreed well, as did measured isoenzyme activities and activities predicted from the amounts of isoenzyme added. MB activities in normal plasma averaged $1.6 \pm 0.28$ U/liter (mean $\pm$ SD).

A packaged kit containing the buffer of low ionic strength, the ion exchange support material, the buffered solution of a strong electrolyte and a filter sampler provides a convenient means for practicing the invention for routine clincal use and is contemplated within the present invention.

The following examples further illustrate the practice of the invention.

EXAMPLE 1

Collection of Blood Samples

Blood was sampled from cardiac patients or from healthy volunteers. Five milliliter samples were collected in tubes containing 20 $\mu$ mol of neutralized ethyleneglycolbis ($\beta$ -aminoethylether)-N,N'-tetraacetic acid and 20 $\mu$ mol of mercaptoethanol, and the plasma was separated and stored at $-20°$ C. with the addition of mercaptoethanol, enzyme activity was decreased by less than 5% after 6months of storage.

Preparation of MM and MB Isoenzymes From Human Myocardium

All steps were performed at 0° C. About 100 g. of myocardium, obtained at necropsy within 12 hours of death, was ground in a chilled meat griner and homogenized in a waring blender in two volumes of a solution containing potassium chloride, 10 mmol/liter, and mercaptoethanol, 1 mmol/liter. After centrifugation (15 min., 600 $\times$ g.) the supernatant fraction was passed through four layers of cheesecloth. Solid ammonium chloride was added to yield a concentration of 0.1 mol/-liter, and the pH was adjusted to 9.0 with concentrated ammonium hydroxide (5 mol/liter). After centrifugation, the precipitate was discarded. Absolute ethanol was added to the supernatant fraction to a final concentration of 400 ml./liter. The precipitate was discarded and the supernate was dialyzed with a Biofiber beaker against Buffer 1, which consisted of tris(hydroxymethyl) aminomethane (50 mmol/liter, pH 7.4), sodium chloride (50 mmol/liter) and mercaptoethanol (1 mmol/liter). A gel marketed under the trade designation "DEAE-Sephadex A50" by Pharmacia, equilibrated in the same buffer, was allowed to settle and excess buffer removed. The moist Sephadex gel and the dialyzed preparation were mixed, 1 g. of hydrated gel being used per 5 mg. of protein. With slow stirring for 40 minutes, the MB isoenzyme was adsorbed to the gel while the MM form remained free. The slurry was filtered on a Buechner funnel through Whatman No. 1 filter paper and the filtrate (low-salt filtrate) containing unadsorbed MM isoenzyme recovered. The gel washed with five volumes of Buffer 1. The MB isoenzyme was desorbed on the Buechner funnel with Buffer 2, which consisted of tris(hydroxymethyl) aminomethane (50 mmol/liter, pH 7.4), sodium chloride (30 mmol/liter), and mercaptoethanol (1 mmol/liter). The high-salt filtrate containing the MB isoenzyme was dialyzed against Buffer 1 and concentrated with the Biofiber device. The low-salt (MM isoenzyme) and high salt (MB isoenzyme) fractions were subjected to a second bath adsorption with the Sephadex gel.

Electrophoretic-fluorometric assay of the isoenzymes in the final filtrates demonstrated no MB activity in the MM fraction and only a trace ($<1\%$) of MM activity in the MB fraction. The MM and MB fractions were dialyzed against a glycine buffer (10 mmol/liter, pH 9.0), concentrated with the hollow-fiber device, and lyophilized. Specific activities (U./mg. protein) of the lyophilized preparations of MM and MB isoenzymes were increased at least 50-fold compared to the specific activities present in the supernatant fraction of the initial homogenate. Recoveries were about 50% for Mm and 28% for MB. The lyophilized preparations could be stored for months at $-20°$ C. with little loss in activity.

Preparation of Extracts From Human Skeletal Muscle and Brain

Skeletal muscle (quadriceps femoris) and brain (cerebrum) from human cadavers were used to prepare crude preparations of MM and BB isoenzymes. The tissues were homogenized in a Waring blender in three volumes of a medium containing potassium chloride, 10 mmol/liter, and mercaptoethanol, 2 mmol/liter. The 15000 $\times$ g. supernatant fractions of these homogenates were recovered and used in pilot experiments designed to explore the feasibility of separating creatine kinase isoenzymes by rapid batch adsorption procedures.

Assay of Creatine Kinase Activity

Creatine kinase activity was assayed spectrophotometrically according to the technique of Rosalki, S.B. Improved procedure for serum creatine phosphokinase determination, J. Lab. Clin. Med. 69, 696 (1967). Activities of less than 5 U./liter were assayed with the recording fluorometer, with use of a number 7–60 primary and a number 3–73 secondary filter. The temperature (30° C.) and reagent (Rosalki reagent) were the same as those used for the spectrophotometric assay. The reaction was started by adding 10- to 100- $\mu$l samples to fluorometric cuvettes containing 1 ml. of reagent. With an activity ranging between 0.5 and 1.0 mU in the cuvette the reaction rate was linear between the fifth and tenth minute of the assay, and measurements were based on the change in fluorescence during this interval. For the measurement of MB activity in plasma from normal individuals, sample size was increased to 200 $\mu$l and reaction time prolonged to 20 minutes. Activities in the cuvettes ranged between 0.05 and 0.1 mU. Measurements of MB activity in normal plasma were at the limit of the useful sensitivity of the fluorometric assay.

Separation of Creatine Kinase Isoenzymes By Electrophoresis on Cellulose Acetate A quantitative fluorometric kinetic assay of creatine kinase isoenzymes separated by electrophoresis on cellulose acetate has been described by Roberts et al. Am. J. Cardiol. 33, 650 (1974). While this procedure is not suitable for rapid processing of numerous samples, it was used in this study as one standard of comparison. Isoenzymes are separated by conventional electrophoresis on cellulose acetate. Segments of the electrophoretic strips encompassing the individual isoenzymes are then incubated with continuous gentle agitation in fluorometric cuvettes containing the reaction mixture. At timed intervals and with the strips removed from the lightpath of the fluorometer, fluorescence readings are taken. Although protein remains to a large extent bound to the cellulose acetate, it behaves enzymatically as if it were free in solution. Under the conditions selected, an enzyme aliquot pipetted directly into the reaction mixture or applied to cellulose acetate, electrophoresed, and assayed in aqueous medium exhibits nearly the same activity.

Separation of Creatine Kinase Isoenzymes By Adsorption With "DEAE-Sephadex A50" Gel "DEAE-Sephadex A50" gel was equilibrated in glycylglycine (20 mmol/liter, pH 9.0, adjusted with sodium hydroxide at 22° C.) and dithiothreitol, 5 mmol/liter, the mixture being called the "glycylglycine buffer". The gel was allowed to settle and excess buffer removed. Half a gram of moist gel was dispensed into a culture tube (1 ml. capacity) and 250 $\mu$l of plasma to be analyzed was added to each tube. The tubes were sealed with Parafilm and rotated for 30 minutes at 2° C. on a Roto-Rack turning at 4 rpm. This mixing procedure was necessary to completely adsorb the MM isoenzyme. After centrifugation for 2 minutes at 600 $\times$ g, the supernatant fraction containing unadsorbed MM(MM supernate) was recovered quantitatively. The gel was washed once with glycylglycine buffer and three times with glycylglycine buffer containing sodium chloride (50 mmol/liter), by filling the tube, mixing by repeated inversion, and recovering the gel by centrifugation. After the fourth centrifugation, glycylclycine buffer and sodium chloride (5 mol/liter) were added to make the sodium chloride concentration 300 mmol/liter in a final volume of 750 $\mu$l. After mixing for 3 minutes on the Roto-Rack, tubes were centrifuged for 2 minutes at 1250 $\times$ g. and the high ionic strength supernate containing desorbed MB isoenzyme (MB supernate) was recovered. Kinase activities in the MM and MB supernates were assayed spectrophotometrically.

Separation of Creatine Kinase Isoenzymes By Adsorption With "DEAE-Glycophase-G" Blass Beads The following solutions were used:
Buffer A: tris(hydroxymethyl) aminomethane (base), 100 mmol/liter; HCl, 56 mmol/liter (pH 8.0 at 22° C.); and dithiothreitol, 3 mmol/liter.
Buffer B: Buffer A with NaCl, 3.8 mol/liter.
The separative procedure involved the following steps all of which were performed at room temperature.

1. Glass beads marketed under the trade designation "DEAE-Glycophase-G" (300 mg., mesh size 120-200, pore size 15 mm) were dispensed into 20 ml. culture tubes (o.d. 16 mm., length 150 mm), and a filter sampler marketed under the trade designation "Unichem" (o.d. 16 mm, length 155 mm) was inserted into each tube. The test tube was then weighed to determine "total dry weight". Weighed tubes could be stored at room temperature indefinitely.

2. Buffer A (1 ml.) was added to each tube followed by the addition of 125 $\mu$l of plasma.

3. The tubes were incubated for 3 minutes on a tilting mixer (for adsorption of MB isoenzyme).

4. The Unichem filter sampler was pushed to the bottom of the tube, minimally compressing the beads and squeezing fluid upward through the filters. The filtered supernatant fraction (MM supernate) was recovered while the beads remained trapped below the filter of the sampler.

5. In order to wash the beads, the Unichem filter sampler was filled to the top with buffer A. By pulling the sampler upward, the buffer was forced through the filter sampler toward the bottom of the tube. Buffer was discarded by inverting the tube. This washing procedure diluted the initial residual fluid in the test tube more than 10-fold. Washing was repeated twice. The entire washing procedure required about 1 minute. The original dilution and washes resulted in approximately a 10,000-fold dilution of MM activity in the initial sample.

6. With the sampler in the down position and with about 1.4 ml. buffer remaining in the tube, each tube was again weighed. The difference between this weight and the initial "total dry weight" yielded the weight (and assuming a relative density of 1, the volume) of fluid present in the tube and sampler.

7. Buffer B, 100 $\mu$l per gram of fluid in the tube, was added to the sampler. The addition of this high-salt, strong electrolyte buffer resulted in desorption of the MB isoenzyme from the glass beads. The fluid phase in the test tube and sampler was thoroughly mixed by moving the sampler up and down two times. The resulting concentration of NaCl was about 390 mmol/liter. The high ionic strength supernatant fraction (MB supernate) was recovered by pushing the sampler down about 2 minutes after the addition of salt.

In further experiments, the gravimetric measurement was eliminated by using graduated tubes, marked to indicate the volume occupied by 1.5 ml. of buffer plus 300 mg. of glass beads. After the washing step, the beads were compacted with the filter sampler, the fluid was pushed back into the sampler and aspirated, and the sampler removed. The tube was then filled to the mark with buffer A containing NaCl, 885 mmol/liter. After dilution with the fluid entrapped in the bead pellet (about 900 $\mu$l) the final concentration of NaCl in the test tube was about 390 mmol/liter. MB supernate could be mixed and recovered by use of a second filter sampler.

Creatine kinase activity in MM and MB supernatant fractions was assayed by the kinetic fluorometric assay previously described. Total creatine kinase activity in plasma samples was measured spectrophotometrically and assumed to represent the sum of the MM and MB activities. Absolute isoenzyme activities were calculated on the basis of the ratio of the fluorometric MM and MB activities and the total activity as measured spectrophotometrically. This calculation assumes BB activity to be negligibly small under most clinical conditions. The correlation between results obtained with fluorometric and spectrophotometric procedures was ascertained daily with serially diluted samples.

Results

MM and MB isoenzyme activities in plasma samples from patients with and without acute myocardial infraction were determined by the electrophoretic fluorometric procedure and isoenzyme activities in the same samples were subsequently determined as described by the "DEAE-Sephadex A50" gel adsorption procedure. Referring to FIG. 1 of the drawings, the results obtained from the two procedures correlated closely. In pilot experiments with mixtures of MB and BB (brain extract) isoenzymes, no salt concentration was found at which desorption of MB was complete without concomitant partial release of BB. Because BB activity is usually negligibly small in human plasma, no special attempts were made to define conditions which would yield complete and rapid separation of the MB and BB isoenzymes. If present, BB isoenzyme activity would therefore be measured as MB activity. The good agreement between the two assay methods suggests that BB activity was negligible in the samples tested and did not result in spurious increases in MB activity by the gel adsorption procedure. The virtual absence of BB activity in plasma (<0.5 U/liter) was confirmed by the electrophoretic fluorometric method in eight samples exhibiting abnormally high MM and MB activities.

Figure 2:
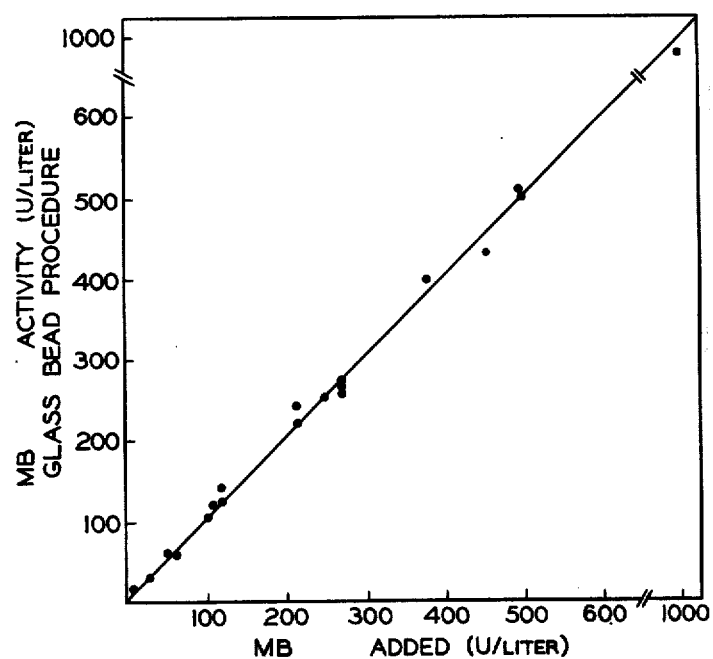
FIG. 2 is a graph illustrating the relationship between the amount of MB isoenzyme added to plasma samples and MB activity measured by the glass bead adsorption procedure of the present invention.

The glass bead absorption procedure of the present invention was evaluated over a wide range of MM and MB activities by constituting test samples through the addition to samples of normal plasma of selected mixtures of MM and MB isoenzymes purified from human myocardium as described. As shown by reference to FIG. 2, within the usual range of activities encountered clinically, MB activity was measured accurately and values did not appear to be influenced by a wide range of MM activities.

Figure 3:
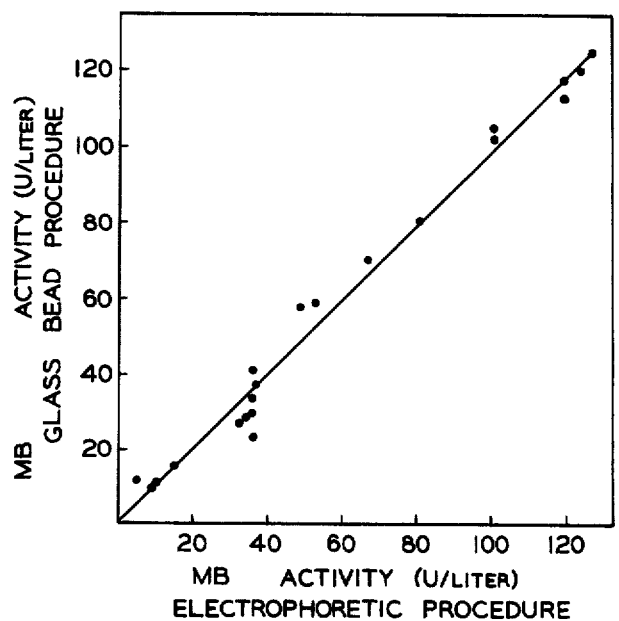
FIG. 3 is a graph illustrating the relationship between MB isoenzyme activity as measured by the electrophoretic kinetic procedure and the glass bead adsorption procedure of the present invention.

In a further evaluation of the glass bead adsorption procedure of the invention, plasma samples from patients with acute myocardial infarction were assayed both with the electrophoretic fluorometric and the glass bead procedures. As shown by reference to FIG. 3, the results obtained with these two procedures agreed closely. In eight samples from patients exhibiting both high MM and MB activities, separation of the isoenzymes with the glass beads was monitored by electrophoresis. After adsorption of the MB isoenzyme (low ionic strength supernate), the electropherograms showed only a MM band. No band in electropherograms of supernates from washing the beads was seen. After desorption (high salt supernate) a single band, in the MB position, was observed. No bands were seen when the electrophoretic strips were incubated without creatine phosphate substrate. In preliminary experiments with mixtures of MM and BB (brain extracts) isoenzymes, no conditions of salt concentration and pH were found under which isoenzyme MB would be completely desorbed without also partially releasing isoenzyme BB. Desorption was therefore carried out at a salt concentration that gave consistently rapid and complete release of MB. Absence of BB bands in the high-salt supernates agrees with previous reports that BB activity is usually not detectable in human plasma. Am. J. Clin. Pathol. 61, 599 (1974).

In order to assess the recovering of activity after adsorption on the glass beads, the total creatine kinase activity in plasma samples was measured fluorometrically and the result compared to the sum of MM and MB activities detected fluorometrically after the isoenzymes were separated by batch adsorption. In 10 samples, the sum of the isoenzyme activities averaged 104 ± 13% (mean ± SD) of the total activity in the initial samples.

In order to determine the precision of the method, plasma samples from patients with acute myocardial infarction were measured in quadruplicate with the results being set out below in Table 1. The sensitivity of the fluorometric assay permitted measurement of MB activity in plasma from normal individuals. In 10 ambulatory men, MB activity was 1.6 ± 0.9 U/liter (means ± SD), in keeping with the results obtained with the electrophoretic fluorometric procedure previously described.

Table 1

Variation of Plasma MM and MB Creatine Kinase Isoenzymes, As Measured by the Glass Bead Method of the Present Invention in Four Samples

| Mean[a] | | Standard Deviation | | Coefficient Variation | |
|---|---|---|---|---|---|
| MM | MB | MM | MB | MM | MB |
| U/liter | | | | % | |
| 48.5 | 5.1 | 2.4 | 0.6 | 4.9 | 12.2 |
| 127.3 | 15.3 | 3.6 | 1.3 | 2.8 | 8.2 |
| 300.5 | 55.2 | 7.4 | 2.1 | 2.4 | 3.7 |
| 541.8 | 19.1 | 19.0 | 4.4 | 3.5 | 5.1 |

[a]Mean of quadruplicate determinations; each sample was analyzed on four different days.

EXAMPLE 2

Preparation of MM and MB Isoenzymes From Human Myocardium

As a first step, human creatine phosphokinase (CPK) isoenzymes were purified to serve as standards and for use in constituting test samples of known isoenzyme composition. CPK isoenzymes were extracted from human myocardium obtained at necrospy; separated, and partially purified as follows: Approximately 100 g. of myocardium was ground in a chilled meat griner, homogenized in two volumes of 10 mM potassium chloride, 1 mM mercaptoethanol in a Waring blender, and centrifuged for 15 minutes at 600 × g. The supernatant fraction was filtered through cheese cloth and precipitated with 0.1 M ammonium chloride after the pH was adjusted to 9.0 with 5 M ammonium hydroxide. After precipitation and centrifugation, ethanol was added to the supernatant fraction in a final concentration of 40%. The precipitate was discarded and the supernatant dialyzed against a buffer consisting of 50 mM tris(hydroxymethyl) aminomethane-HCl, pH 7.4, with 1 mM mercaptoethanol with the use of a Biofiber 80 beaker at a flow rate of 100 ml./min. for 30 minutes. This fraction contained both the MM and MB CPK isoenzymes. The MM and MB isoenzymes were separated by repetitive batch adsorption with "DEAE-Sephadex A50" gel equilibrated with 50 mM MaCl, 50 mM tris(hydroxymethyl) aminomethane-HCl, pH 7.4, and 1 mM mercaptoethanol as previously described. One ml. of gel/4.8 mg. protein was used. Under these conditions, MM remained in the filtrate and MB was adsorbed to the gel. After extensive washing of the gel with the same buffer, the MB isoenzyme bound was desorbed with buffer containing 30 mM NaCl, recovered by filtration, and dialyzed against a low salt medium to avoid inactivation of CPK activity by prolonged exposure to high concentrations of salt. The concentrated dialysate, containing the MB isoenzyme free from MM, was lyophilized and stored at −20 C.

Assay of CPK Isoenzyme Activity in Serum Samples

CPK activity was assayed fluorometrically with the Rosalki procedure, J. Lab Clin. Med. 69: 696 (1967). Polycarbonate centrifuge tubes (50 ml.) containing dry "DEAE-Glycophase-G" glass beads (300 mg.; mesh size 120–200) were preweighed. One ml. of buffer containing 100 mM tris (hydroxymethyl)methane-HCl, pH 8.0, and 3 mM dithiothreitol followed by 0.125 ml. of the sample to be analyzed were added to the tube. MB CPK was adsorbed completely by equilibration for 3 minutes. After sedimentation of the beads, the supernatant fraction containing MM CPK was recovered quantitatively. The beads were washed twice with 45 ml. of buffer.

The MB CPK isoenzyme was desorbed from the glass beads by adding 100 $\mu$l of 3.8 M NaCl per gram of residual aqueous phase in the preweighed tube and agitating the mixture for 2 minutes. The high ionic strength supernatant fraction contained desorbed MB CPK isoenzyme. Under the conditions used, when the serum samples were constituted with human MB and MM CPK (isolated with myocardium) in a ratio of 1:10, over a range of 50 to 741 ml. U/ml. total activity, the recovery of MB activity averaged 97% (N=15).

The reproducibility of the assay was examined in samples from patients with acute myocardial infarction as follows: each sample was assayed five times. A total of nine different samples (with average MB, activity = 5, 19, 37, 49, 52, 54, 78, 96, 103 ml. U/ml.) were evaluated. In each case, the standard deviation of the five determinations was 4% or less of the mean MB activity in that particular sample.

Results

Figure 4:
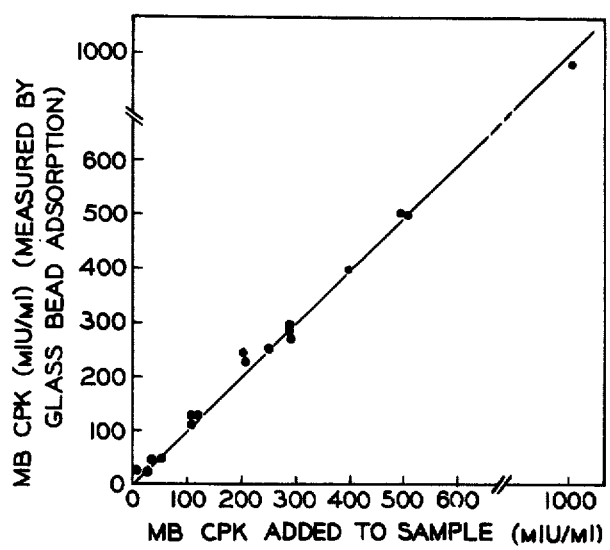
FIG. 4 is a graph illustrating the results of quantitative assay of CPK isoenzymes by the glass bead adsorption procedure of the present invention.

When serum samples were constituted with purified human MM and MB CPK isoenzymes to produce known combinations of activity of each, the results shown in FIG. 4 were obtained. As can be seen, the relationship between MB CPK activity added to the sample and observed activity detected with the adsorption assay method of the present invention was close over a wide range of MB CPK activity. In the experiments shown, MB CPK represented from 10 to 80% of total CPK activity, over a wide range of total activity in the sample.

Figure 5:
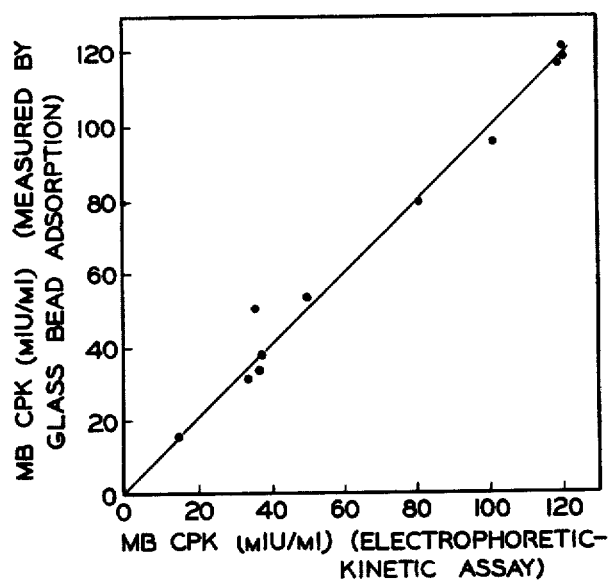
FIG. 5 is a graph illustrating the results of CPK isoenzyme assays performed with the glass bead adsorption procedure of the present invention compared to results obtained with a previously standardized electrophoretic kinetic assay.

As shown in FIG. 5, the amount of MB CPK determined by the assay procedure of the present invention in samples from patients with acute myocardial infarction correlated closely with MB activity measured with the laborious electrophoretic-kinetic technique previously described. Thus, the present invention permits rapid, quantitative assessment of MB CPK activity over a range from <5 1000 m I.U./ml.

EXAMPLE 3

Separation of MM and MB Isoenzymes in Human Serum

Human sera was collected after blood samples were clotted and centrifuged. The sera collected were frozen immediately until they were ready for use.

200 $\mu$l of sera was added to a test tube with 150 mg. of glass beads marketed under the trade designation "DEAE-Glycophase-G" followed by the addition of 500 $\mu$l of Buffer A from Example 1. The contents were mixed well for approximately 30 seconds and a filter sampler was inserted and the filtrate collected in accordance with the procedure described in Example 1. The filtrate contained the MM isoenzyme.

The glass beads were then washed three times with approximately 4 ml. of Buffer A from Example 1 and the final volume of the solution was adjusted to 0.65 ml. as described in Example 1.

The MB isoenzyme was then released by addition of 50 $\mu$l of a 3.0 M sodium chloride solution followed by mixing of the tube for 30 seconds. The separated MM and MB fractions were assayed for CPK activity with an auto analyzer marketed under the trade designation "ABA-100 Chemistry Auto Analyzer".

The MB content of myocardial infarction suspected patient samples were also analyzed independently by an electrophoretic method.

The results are as follows:

|  | MB Activity Measured by the Method of the Present Invention | MB Activity Measured by Electrophoretic Method |
|---|---|---|
| Normal Person 1 | 1.3 | Negative |
| Normal Person 2 | 2.6 | Negative |
| Normal Person 3 | 0.8 | Negative |
| Myocardial Infarction Suspected Patient |  |  |
| 1 | 5.9 | Trace |
| 2 | 6.2 | Trace |
| 3 | 5.8 | Trace |
| 4 | 98.3 | Positive |
| 5 | 8.3 | Positive |
| 6 | 21.7 | Positive |
| 7 | 13.2 | Positive |
| 8 | 35.9 | Positive |
| 9 | 7.9 | Positive |

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. An in vitro method for effecting rapid separation of the MM and MB creatine kinase isoenzymes in blood plasma or serum and for determining the relative activities of the thus separated isoenzymes comprising the steps of contacting a blood plasma or serum sample and a buffer of low ionic strength with an ion exchange support comprising porous glass beads having a stationary phase coupled to the surfaces thereof through an intermediate coupling agent;

incubating the resultant mixture to effect MB isoenzyme adsorption by said support;

separating the supernatant liquid fraction containing the MM isoenzyme from said support;

washing the support to effect removal of residual MM;

adding a buffered solution of a strong electrolyte to said support to effect desorption of the MB isoenzyme therefrom;

separating the supernatant liquid fraction containing the MB isoenzyme from said support; and assaying the MM and MB activity in the respective liquid fractions thus obtained.

2. An in vitro method as set forth in claim 1 wherein said intermediate coupling agent is a silane coupling agent constituted by an organosilane with a silicon functional group capable of bonding to the surface of the glass beads and an organic functional group capable of bonding to the stationary phase.

3. An in vitro method as set forth in claim 2 wherein said organic functional group is a simple carbohydrate or carbohydrate derivative.

4. An in vtro method as set forth in claim 3 wherein said organic functional group is glycerol.

5. An in vitro method as set forth in claim 2 wherein said intermediate organosilane coupling agent is glycidoxypropyltrimethoxysilane.

6. An in vitro method as set forth in claim 2 wherein said stationary phase is derived from diethylamine or diethylaminoethanol.

7. An in vitro method as set forth in claim 1 wherein said intermediate coupling agent is formed from a Grignard reagent of the formula RMgX where R is lower alkenyl and X is halogen.

8. An in vitro method as set forth in claim 7 wherein said Grignard reagent is 1-butenyl magnesium bromide.

9. An in vitro method as set forth in claim 1 wherein the buffer of low ionic strength has a pH between approximately 7.1 and 9.0.

10. An in vitro method as set forth in claim 1 wherein the concentration of strong electrolyte in said buffered solution is between approximately 250 and 500 mmol/liter.

11. An in vitro method as set forth in claim 10 wherein the electrolyte is sodium chloride.

12. An in vitro method as set forth in claim 1 wherein the sample is blood plasma and the step of washing the support to effect removal of residual MM results in at least approximately a 1000 fold dilution of MM activity in the initial blood plasma sample.

13. An in vitro method as set forth in claim 1 wherein the resultant mixture from the first step is incubated for approximately three minutes.

14. An in vitro method as set forth in claim 1 wherein said incubating and separating steps are carried out by means of a filter sampler.

* * * * *